US012364391B2

(12) United States Patent
De Rossi et al.

(10) Patent No.: US 12,364,391 B2
(45) Date of Patent: Jul. 22, 2025

(54) METHOD AND SYSTEM FOR DETERMINING A PRESCRIPTION FOR AN EYE OF A PERSON

(71) Applicant: Essilor International, Charenton-le-Pont (FR)

(72) Inventors: Hélène De Rossi, Charenton-le-Pont (FR); Marius Peloux, Charenton-le-Pont (FR); Stéphane Boutinon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 638 days.

(21) Appl. No.: 17/771,376

(22) PCT Filed: Oct. 22, 2020

(86) PCT No.: PCT/EP2020/079790
§ 371 (c)(1),
(2) Date: Apr. 22, 2022

(87) PCT Pub. No.: WO2021/078880
PCT Pub. Date: Apr. 29, 2021

(65) Prior Publication Data
US 2022/0361745 A1 Nov. 17, 2022

(30) Foreign Application Priority Data
Oct. 24, 2019 (EP) .................................. 19306384

(51) Int. Cl.
*A61B 3/103* (2006.01)
*A61B 3/00* (2006.01)
*A61B 3/14* (2006.01)

(52) U.S. Cl.
CPC ............ *A61B 3/103* (2013.01); *A61B 3/0008* (2013.01); *A61B 3/14* (2013.01)

(58) Field of Classification Search
CPC ......... A61B 3/103; A61B 3/0008; A61B 3/14; A61B 3/0025; A61B 3/028
(Continued)

(56) References Cited

U.S. PATENT DOCUMENTS 9,733,460 B2 * 8/2017 Kang ................. G02B 21/0064
11,205,069 B1 * 12/2021 Sharma ............... G06V 10/143
(Continued)

FOREIGN PATENT DOCUMENTS

CN 107890336 A 4/2018
CN 107920731 A 4/2018
(Continued)

OTHER PUBLICATIONS

International Search Report and Written Opinion issued Dec. 15, 2020 in PCT/EP2020/079790 filed on Oct. 22, 2020, 12 pages.
(Continued)

*Primary Examiner* — Mohammed A Hasan
(74) *Attorney, Agent, or Firm* — Oblon, McClelland, Maier & Neustadt, L.L.P.

(57) ABSTRACT

A system for determining a prescription for an eye of a person, the system being configured to communicate with a mobile device including at least one first light source adapted to illuminate the eye with first light having a first optical wavelength, at least one second light source adapted to illuminate the eye with second light having a second optical wavelength different from the first wavelength, and a processor that measures the photorefraction of the eye at the first wavelength based on at least one picture of the eye recorded when illuminating the eye with first light, measures the photorefraction of the eye at the second wavelength based on at least one picture of the eye recorded when illuminating the eye with second light, determines the prescription for the eye based on the measured photorefraction
(Continued)

at the first wavelength and the measured photorefraction at the second wavelength.

20 Claims, 5 Drawing Sheets

(58) Field of Classification Search
    USPC .......................................................... 351/221
    See application file for complete search history.

(56) References Cited

U.S. PATENT DOCUMENTS

| | | | |
|---|---|---|---|
| 2012/0320340 | A1 | 12/2012 | Coleman, III |
| 2013/0083185 | A1 | 4/2013 | Coleman, III |
| 2016/0026253 | A1* | 1/2016 | Bradski ................ H04N 13/128 345/8 |
| 2016/0120402 | A1 | 5/2016 | Limon |
| 2017/0079523 | A1 | 3/2017 | Limon |
| 2017/0150882 | A1 | 6/2017 | Lindig et al. |
| 2017/0164827 | A1 | 6/2017 | Lindig et al. |
| 2017/0188813 | A1 | 7/2017 | Arnold et al. |
| 2019/0125181 | A1 | 5/2019 | Lindig et al. |
| 2019/0307324 | A1 | 10/2019 | Limon |
| 2022/0304572 | A1* | 9/2022 | Coveney .................. G06T 7/60 |
| 2023/0367857 | A1* | 11/2023 | Haller .................... G06V 40/14 |
| 2023/0377370 | A1* | 11/2023 | Haller ................. G06V 10/993 |

FOREIGN PATENT DOCUMENTS

| | | |
|---|---|---|
| WO | WO 2012/177544 A1 | 12/2012 |
| WO | WO 2019/099952 A1 | 5/2019 |

OTHER PUBLICATIONS

Schaeffel et al., "Infrared photoretinoscope", Applied Optics, vol. 26, No. 8, Apr. 15, 1987, pp. 10505-1509 (Total 5 pages).

Wesemann et al., "Theory of eccentric photorefraction (photoretinoscopy): astigmatic eyes", J. Opt. Soc. Am. A, vol. 8, No. 12, Dec. 1991, pp. 2038-2047 (Total 10 pages).

Cole, "Multimeridian Photorefraction: a Technique for the Detection of Visual Defects in Infants and Preverbal Children", Johns Hopkins APL Technical Digest, vol. 12, No. 2, 1991, pp. 166-175 (Total 10 pages).

Roorda et al., "Geometrical theory to predict eccentric photorefraction intensity profiles in the human eye", J. Opt. Soc. Am. A, vol. 12, No. 8, Aug. 1995, pp. 1647-1656 (Total 10 pages).

Roorda et al., "Slope-based eccentric photorefraction: theoretical analysis of different light source configurations and effects of ocular aberrations", J. Opt. Soc. Am. A, vol. 14, No. 10, Oct. 1997, pp. 2547-2556 (Total 11 pages).

Chen et al., "Simulation of eccentric photorefraction images", Optics Express, vol. 11, No. 14, Jul. 14, 2003, pp. 1628-1642 (Total 15 pages).

Wu et al., "Two-dimensional simulation of eccentric photorefraction images for ametropes: factors influencing the measurement", Ophthalmic & Physiological Optics, vol. 38, 2018, pp. 432-446 (Total 15 pages).

Nakajima et al., "Verification of the lack of correlation between age and longitudinal chromatic aberrations of the human eye from the visible to the infrared", Biomedical Optics Express, vol. 6, No. 7, Jul. 1, 2015, pp. 2676-1694 (Total 19 pages).

Combined Chinese Office Action and Search Report issued Nov. 22, 2024, in corresponding Chinese Patent Application No. 202080069152.0 (with English Translation), 10 pages.

\* cited by examiner

METHOD AND SYSTEM FOR DETERMINING A PRESCRIPTION FOR AN EYE OF A PERSON

FIELD OF THE INVENTION

The invention relates to a method and a system for determining a prescription for an eye of a wearer. The invention further relates to corresponding computer program product and computer readable medium. The invention further relates to a method for providing an ophthalmic lens adapted to a prescription of the wearer.

BACKGROUND OF THE INVENTION

An optical lens is generally determined to be then manufactured in accordance with the wearer specifications. In the case, for example, of an ophthalmic lens for the correction or improvement of eyesight, the ophthalmic lens is determined according to a wearer prescription corresponding to the visual requirements of that wearer.

The prescription of an eye of a person can be determined by measuring the refraction of the eye also called photorefraction or photoretisnoscopy. The principle of photorefraction involves projecting light into the eye during flash photography and then examining the paths of light that emerge from the pupil after scattering on the back portion of the interior of the eyeball.

For example for a myopic wearer, light coming from a light source and reflected on the retina enters a camera in such a way that the camera sees a "crescent" inside the pupil of the person. The size, position and shape of this crescent depend on the refraction of the wearer's eye. For given distance between the light source and the edge of the camera aperture, also called eccentricity, working distance, camera lens diameter and pupil diameter, the size of the crescent is proportional to the refractive error. Consequently, a power, astigmatism and axis can be determined based on measurements of the refractive error in at least three different meridians defined by the axis crossing the center of the camera and the light source (Cf. "Two-dimensional simulation of eccentric photorefraction images for ametropes: factors influencing the measurement", Y. Wu, L. N. Thibos & T. R. Candy, Ophthalmic Physiol. Opt. 2018; 38: 432-446).

Today's optometrists use accurate but cumbersome devices which require a rather long and not practical measurement to evaluate the prescription of a wearer.

Particularly in developing countries, optometrists are likely to be rare and rather low-skilled, and may not be able to afford expensive prescription measurement needs.

One object of the present invention is to provide a cheap, simple and very quick prescription measurement method and system.

SUMMARY OF THE INVENTION

To this end, the invention proposes a system for determining a prescription for an eye of a person, the system being configured to communicate with a mobile device, comprising:
 at least one first light source adapted to illuminate the eye with first light having a first optical wavelength;
 at least one second light source adapted to illuminate the eye with second light having a second optical wavelength different from the first wavelength; and
 a calculation module comprising a memory and a processor arranged to execute a program instructions stored in the memory to:
  measure the photorefraction of the eye at the first wavelength based on at least one picture of the eye recorded when illuminating the eye with first light;
  measure the photorefraction of the eye at the second wavelength based on at least one picture of the eye recorded when illuminating the eye with second light;
  determine the prescription for the eye based on the measured photorefraction at the first wavelength and the measured photorefraction at the second wavelength.

Advantageously, such system allows non-invasive, easy-to-use, cheap tool to perform digital refraction measurements, particularly in developing countries. In the sense of the invention, digital refraction measurement is refraction measurement using digital means.

Indeed, while certain range of wavelength, also called "dark zone", of a light source flashing on the eye may cause no crescent for corresponding certain refractive error, the system allows the simultaneous objective measurement of the refraction of an eye of a person at two wavelengths and consequently its prescription. Consequently, there is always a possible measurement of the refraction since at least one picture under one of both light sources should show the crescent.

In addition, the system can be advantageously removably fastened to and associated with a mobile device like a smartphone.

According to further embodiments which can be considered alone or in combination:
 the calculation module is embedded into the mobile device;
 the system for determining a prescription is further configured to be in communication with a distant unit comprising a memory and a processor arranged to execute a program instructions stored in the memory to store data relative at least to the measured photorefraction of the eye at the first wavelength, the measured photorefraction of the eye at the second wavelength;
 the system is fastened to a housing of the mobile device and removable;
 the or each first light source is configured to emit infrared or near infrared light and the or each second light source is configured to emit visible light;
 the system is configured to be in communication with a camera adapted and configured to record at least one picture of the eye of the person when the eye is illuminated by first light or second light;
 the camera is embedded into the mobile device;
 the camera is embedded into the system;
 the second light source is arranged at the same distance from the camera than the first light source;
 the system for determining the prescription of the eye comprises at least one set of three first light sources, each adapted to emit first light at the first optical wavelength;
 the first light sources of each set are equidistant from the camera and are arranged so as to define three directions regularly spaced angularly;
 the processor is arranged to execute a program instructions stored in the memory to:
  illuminate the eye with first light emitted successively by the or each first light source emitting at the first wavelength, illuminate the eye with second light by the second light source emitting at the second wavelength, recording at least one picture of the eye of the person by the camera when the eye is illuminated by first light and/or second light;

the system comprises a plurality of sets of three first light sources, the distance between the camera and the first light sources of a set is different from one set to another, the first light sources of the plurality of the sets are arranged so as to define the same three directions regularly spaced angularly, and wherein the processor is arranged to execute a program instructions stored in the memory to measure the photorefraction of the eye at the first wavelength by illuminating the eye with first light emitted successively by each first light source of at least one set of the plurality of sets before measuring the photorefraction of the eye at the second wavelength by illuminating the eye with second light emitted by the second light source;

the system comprises a plurality of second light sources adapted to emit light having the second optical wavelength; each second light source being equidistant from the camera and associated to one different direction define by a first light source and the camera, and wherein the processor is arranged to execute a program instructions stored in the memory to select one of the second light sources to illuminate the eye before the measurement of the photorefraction of the eye at the second wavelength based on the measurement of the photorefraction of the eye at the first wavelength;

the system comprises a plurality of second light sources adapted to emit light having the second optical wavelength; each second light source being at different distance from the camera and associated to the same direction define by a first light source and the camera, and wherein the processor is arranged to execute a program instructions stored in the memory to select one of the second light sources to illuminate the eye before the measurement of the photorefraction of the eye at the second wavelength based on the measurement of the photorefraction of the eye at the first wavelength.

Another object of the invention is directed to a method for determining a prescription for an eye of a person with a system according to the invention, the method comprising at least:

measuring the photorefraction of the eye at the first wavelength based on at least one picture of the eye recorded when illuminating the eye with first light emitted successively by the or each first light source;

measuring the photorefraction of the eye at the second wavelength based on at least one picture of the eye recorded when illuminating the eye with second light emitted by the second light source; and determining the prescription for the eye based on the measured photorefraction at the first wavelength and the measured photorefraction at the second wavelength.

According to further embodiments of the method which can be considered alone or in combination:

measuring the photorefraction of the eye at the second wavelength and measuring the photorefraction of the eye at the first wavelength are spaced temporally by less than 0.5 s;

the method further comprises determining the distance between the eye of the person and the camera;

the method further comprises determining the interpupilliary distance (IPD) of the person;

the method further comprises determining the orientation of the system in relation to the eyes of the person;

measurements are made preferably in a dark environment.

The invention further relates to a method for providing an ophthalmic lens adapted to a prescription of the wearer, the method comprising:

determining a prescription for an eye of the wearer according to the previous method of the invention; and manufacturing the ophthalmic lens according to the determined prescription adapted to the eye of the wearer.

According to a further aspect, the invention further relates to a computer program product comprising one or more stored sequence of instructions that are accessible to a processor and which, when executed by the processor, causes the processor to carry out the steps of the method for determining a prescription for an eye of the wearer according to the invention, and more particularly at least the steps of:

measuring a photorefraction of an eye at a first wavelength based on at least one picture of the eye recorded when illuminating the eye with first light emitted by the or each first light source;

measuring a photorefraction of the eye at a second wavelength based on at least one picture of the eye recorded when illuminating the eye with second light emitted by a second light source;

determining a prescription for the eye based on the measured photorefraction at the first wavelength and the measured photorefraction at the second wavelength.

The invention also relates to a computer-readable storage medium having a program recorded thereon; where the program makes the computer execute at least the method of the invention.

The invention also relates to a computer readable medium carrying one or more sequences of instructions of the computer program product according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION OF PREFERRED EMBODIMENTS

The invention relates to a method and a system for determining a prescription for an eye of a person. Such system is adapted and configured to implement the method for determining a prescription for an eye of a person according to the invention.

The prescription comprises a set of optical characteristics such as spherical power, cylindrical power, cylinder axis, addition power, and prescribed prism, determined by an ophthalmologist in order to correct the vision defects of the wearer.

Figure 1:
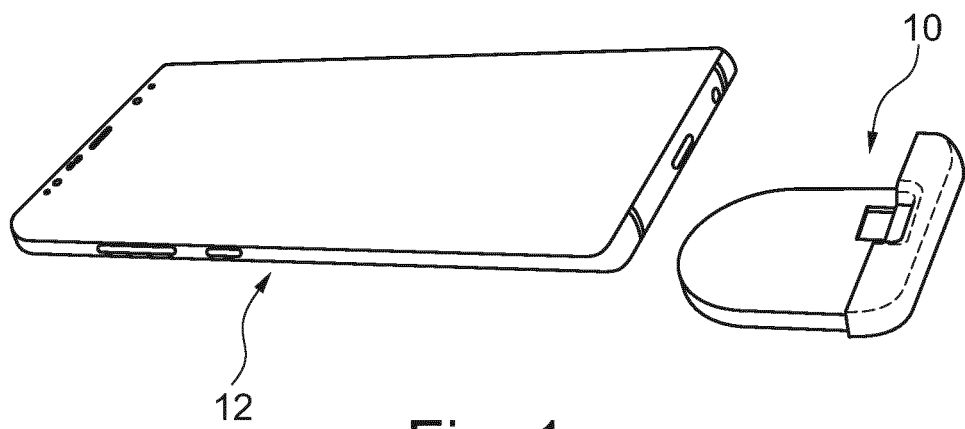
FIGS. 1 and 2 is a perspective view of a system for determining the prescription of an eye of a person according to the invention.
Figure 2:
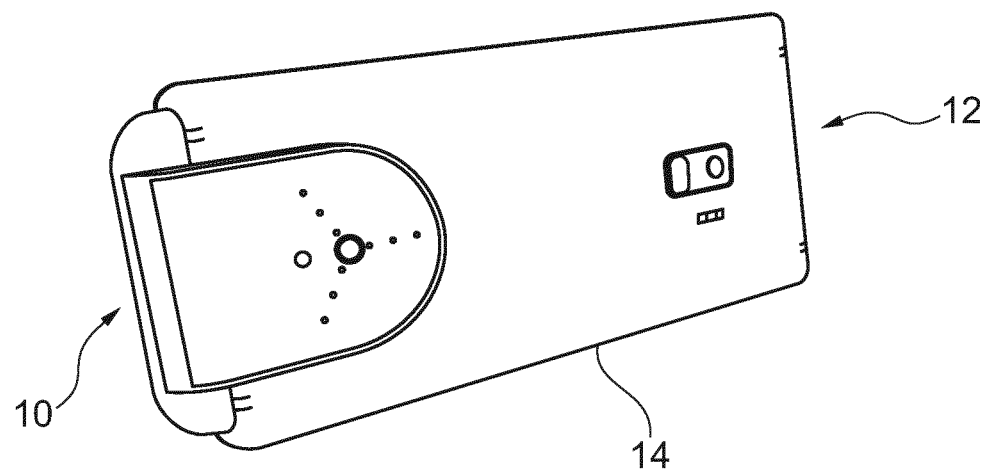

With reference to FIGS. 1 and 2, the system 10 according to the invention is configured to communicate with a mobile device 12, in particular a smartphone. For example, the system 10 can communicate with or via the mobile device 12 in a wired or wireless manner.

Preferably, the system is adapted to be fastened to a housing 14 of the mobile device 12 as illustrated on FIGS. 1 and 2.

The system 10 is illustrated before being fastened to the mobile device 12 on FIG. 1 and after being fastened to a housing 14 of the mobile device 12 on FIG. 2.

In the following description, smartphones are used as examples of such mobile system. Nevertheless, other mobile systems can also be used such as tablet personal computers or laptop computers.

Figure 3:
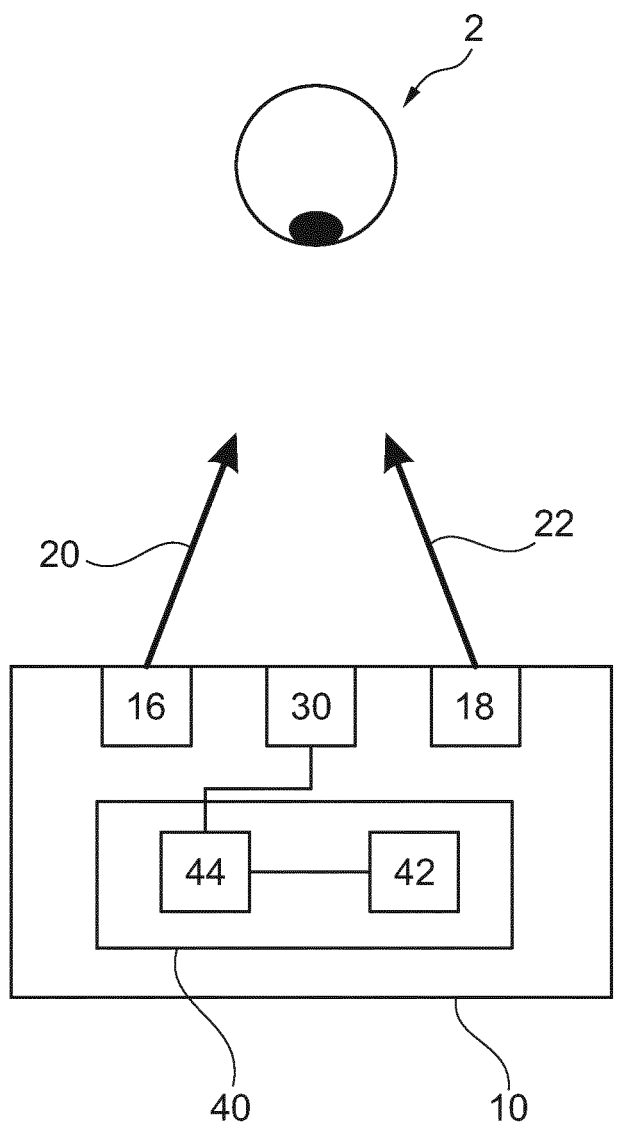
FIG. 3 is a schematic diagram of a system adapted to determine the prescription of an eye of a person according to a first embodiment of the invention.

FIG. 3 shows a schematic illustration of the system 10 according to a first embodiment of the invention.

The system 10 comprises a first light source 16 and a second light source 18. The first and second light sources 16, 18 are each adapted to illuminate an eye 2 of the person with respectively first light 20 having a first optical wavelength and second light 22 having a second optical wavelength. The second optical wavelength is different from the first optical wavelength.

Each of the first and second light sources 16, 18 may be configured to illuminate the eye directly or indirectly, for example by being reflected by a mirror.

Preferably, the first light source is configured to emit infrared or near infrared light so as not to change the pupil diameter during a refraction measurement and thus, the prescription determining.

The second light source is preferably configured to emit visible light, for example configured to emit green light at around 550 nm. Visible light allows overcoming the drawback of the shift in the prescription determining induced by using infrared light and the fact that the eye is very chromatic.

The second light source may be configured to emit red light allowing a better reflection of the retina.

Preferably, the light sources are light-emitting diode (LED). Preferably the bandwidth of the spectrum of the light sources is very narrow, less than 50 nm at half width.

Infrared LEDs with different spectral bands could also be considered for more accurate extrapolation of a model of the prescription function of the wavelength.

The system 10 further comprises a camera 30 adapted and configured to record at least one picture of the eye of the person when the eye is illuminated by first light or second light.

A very narrow band pass filter, i.e. less than 50 nm at half width, could be applied to the camera so that the camera only collects infrared signal from the sources and their reflections on the retina, not from the sun or from any incandescent lamp for instance, that could affect the measurement results, when one of the used wavelength is infrared. Alternatively, the filter may also be a high-pass filter, with no light other than infrared light passing.

Preferably, the camera is embedded in the system 10 such that it can acquire picture of the eye of the person in "selfie" mode or in "standard photo" mode. The person could also take a picture of himself in front of a flat mirror to perform his/her refraction measurement.

In addition, the system could also be inclined in relation to the smartphone to meet a best ergonomic needs.

While in the preferred embodiment, the camera is embedded in the system, the camera can be embedded in the smartphone and the system is configured to be in communication with the camera of the smartphone and arranged such that the camera of the smartphone can record pictures of the eye of the person when the eye is illuminated by first light or second light.

Preferably, the second light source 18 is arranged at the same distance as the first light source 16 from the camera 30. The distance between the first light source or the second light source and the camera is preferably comprised between 0 and 30 mm.

The system further comprises a calculation module 40 comprising a memory 42 and a processor 44 arranged to execute a program instructions stored in the memory to implement the method for determining a prescription for an eye of a person according to the invention.

Figure 4:
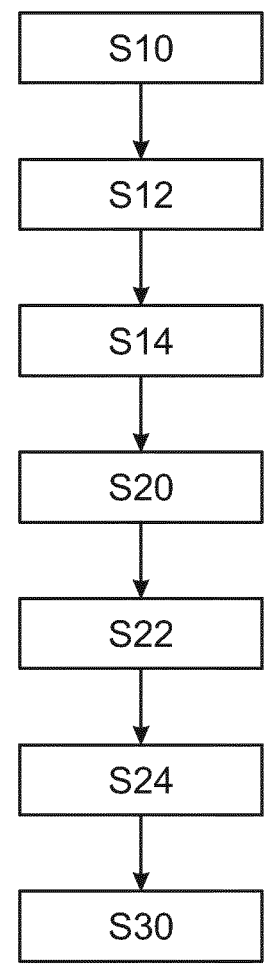
FIG. 4 is an illustration of a chart-flow of a method for determining a prescription of an eye of a person according to the first embodiment of the invention.

With reference to FIG. 4, the method comprises:
- a first illuminating step S10,
- a first acquisition step S12
- a first photorefraction measuring step S14,
- a second illuminating step S20,
- a second acquisition step S22
- a second photorefraction measuring step S24,
- a prescription determining step S30.

During the first illuminating step S10, the eye 2 of the person is illuminated with first light 20 having the first optical wavelength by the first light source 16.

Then, at least one first picture is acquired by the camera 30 and recorded when illuminating the eye 2 with first 20 light in S12.

During the first photorefraction measuring step S14, the photorefraction of the eye at the first wavelength is measured based on the first picture(s) of the eye recorded when illuminating the eye with first light.

Photorefraction is an objective refraction method based on a picture of light reflection by the retina. The refractive state can be calculated from the magnitude and position of this light reflection using a mathematical formula or from a physical simulation model.

During the second illuminating step S20, the same eye 2 of the person is illuminated with second light 22 having the second optical wavelength by the second light source 18.

Then, at least one second picture is acquired by the camera 30 and recorded when illuminating the eye 2 with second light in S22.

During the second photorefraction measuring step S24, the photorefraction of the eye at the second wavelength is measured based on the at least one second picture of the eye recorded when illuminating the eye with second light.

The second illuminating step should follow quickly the first illuminating step, i.e. fast enough so that the eye pupil has not time to reduce to ensure a large size of pupil and to avoid eye movements, eye blinks . . . . Preferably, measuring the photorefraction of the eye at the second wavelength and measuring the photorefraction of the eye at the first wavelength are spaced temporally by less than 0.5 s.

Then, the prescription for the eye is determined based on the measured photorefraction at the first wavelength and the measured photorefraction at the second wavelength in S30.

More particularly, the measured power at the first wavelength and the measured power at the second wavelength may be compared and used to correct the first refraction measurement of the person's eye to determine the prescription of the person's eye.

Alternatively, it is possible to mix the above individualized first and second refraction measurements with an average correction table via a weighting function.

Preferably, the calculation module 40 is embedded into the smartphone 12. Alternatively, the calculation module 40 may be embedded into the system 10. Thus, the refraction measurements and the prescription determining are performed via a local analysis within an application that applies pattern recognition algorithms for measuring the size, position and shape of the crescent, as well as the pupil diameter.

Nevertheless, the calculation module 40 may be embedded at least partly into the mobile device 10 and/or the smartphone 12 and/or a distant unit (not illustrated).

Indeed, the system 10 for determining a prescription may further be configured to be in communication with a distant unit comprising a memory and a processor arranged to execute a program instructions stored in the memory to store data relative at least to the measured photorefraction of the eye at the first wavelength, the measured photorefraction of the eye at the second wavelength. Then, the determining of the prescription of the eye S30 may also be implemented by the distant unit when the processor of the distant unit executes a corresponding program instructions stored in the memory of the distant unit. In this case, the measured data is stored in a cloud, recognition and/or machine learning algorithms are used for analyzing the results. In this case person accounts could be created to track the evolution of the prescription of a person with correlated graphics in an application.

Measurements are preferably made in a low light environment to expand the person's pupil to a maximal value, which reduces the width of the dark zone.

Furthermore, the method may advantageously comprises a step for determining the distance between the eye of the person and the camera. The distance measurement can be made thanks to a simple 1-pixel time-of-flight (ToF) sensor or to a ToF pixel array. Nevertheless, a sensor measuring the quantity of light reflected from the measured object may also be used to determine the distance between the eye of the person and the camera.

The distance may also be determined thanks to a stereoscopic combination of images acquired from the camera of the smartphone and images acquired from the camera of the system. The distance may also be determined thanks to the front or rear camera of the Smartphone or the camera of the system and an associated image processing. For example, the distance could be estimated considering that the iris size is approximately the same for everybody. In another embodiment, the person using the system may wear some goggles whose size is well-known, as a reference to estimate the distance between the eye and one of the camera.

The method may further advantageously comprises a step for determining the interpupilliary distance (IPD) of the person.

Advantageously, the method may further comprises a step for determining the orientation of the system in relation to the eyes of the person in order to determine precisely the axis of the astigmatism. This orientation may be determined using the inertial motion unit (IMU) of the smartphone. Another way to evaluate this orientation is to evaluate the angle of the line separating the two eye centers in relation to an axe defined between a normal axis to the aperture of the camera of the system and the line separating the two eye centers.

In addition, while in the embodiment as presently described, the first photorefraction measuring step S14 is implemented before the second illuminating step S20 and the second acquisition step S22, it will be understood, that in alternative embodiments of the invention, the photorefraction measurement at the first wavelength may be implemented after all acquisitions at first and second wavelengths are performed in order to reduce the measurement time since the photorefraction measurement steps can may take some time.

Figure 5:
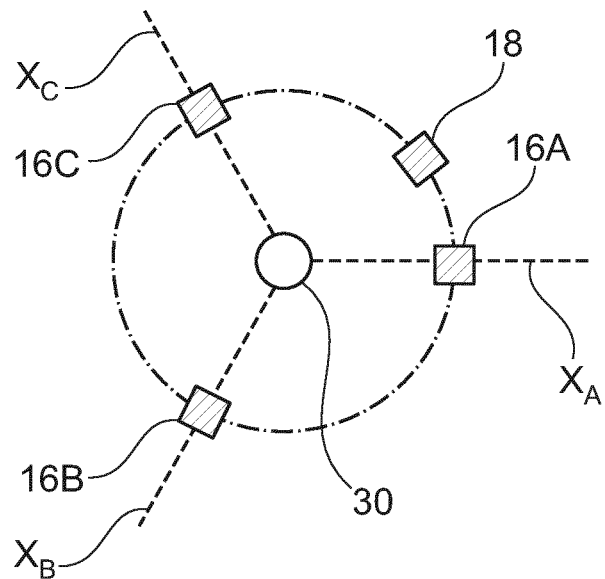
FIG. 5 shows an illustration of a light sources arrangement which can be used in a system for determining the prescription of an eye according to a second embodiment of the invention.

FIG. 5 illustrates a second and preferred embodiment of the system according to the invention. This second embodiment differs from the previous one in that the system comprises a set of three first light sources 16A, 16B and 16C, each adapted to illuminate the eye 2 of the person with respectively first light 20 having the first optical wavelength.

In this preferred embodiment, the system still has only one second light source 18.

The first light sources 16A, 16B and 16C of the set are arranged to be equidistant from the camera 30 and to define three directions regularly spaced angularly also called meridians $X_A$, $X_B$ and $X_C$.

Furthermore, the second light source 18 is preferably arranged at the same distance than the first light source 16 from the camera 30.

According to this second embodiment, the processor 44 is arranged to execute a program instructions stored in the memory 42 to implement a second embodiment of the method for determining the prescription of the eye of the person according to the invention.

Figure 6:
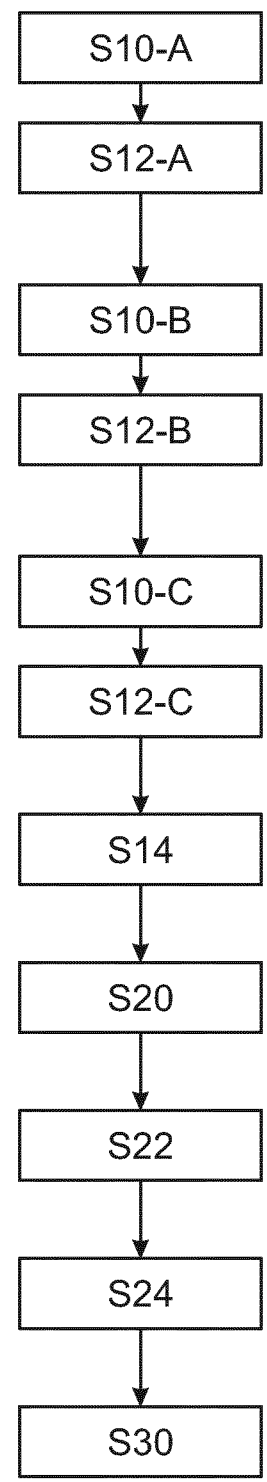
FIG. 6 is an illustration of a chart-flow of a method for determining a prescription of an eye of a person according to the second embodiment of the invention.

With reference to FIG. 6, the second embodiment of the method differs from the previous one in that the step S10 for illuminating the eye with first light and the step S12 for acquiring and recording the corresponding first pictures by the camera when the eye is illuminated with first light are repeated successively for each first light source 16A, 16B and 16C of the set. The step for illuminating the eye by the first light source 16K is denoted S10-K and the step for acquiring and recording the corresponding first pictures by the camera when the eye is illuminated by the first light source 16K is denoted S12-K, K being A, B or C. Thus, the photorefraction of the eye at the first wavelength is measured before measuring the photorefraction of the eye at the second wavelength by illuminating the eye with second light emitted by the second light source.

In other words, all the measurements at the first wavelength are done before the single measurement at the second wavelength.

Such second embodiment allows an accurate measurement of eye refraction at infrared wavelength thanks to the measurements in three directions $X_A$, $X_B$ and $X_C$ and for several distances between the set of first light sources and the camera and consequently, an accurate determining of the prescription for the eye of the person. Indeed, thanks to the measurements in three directions $X_A$, $X_B$ and $X_C$ the complete refraction may be determine, i.e. power, astigmatism and axis.

Figure 7:
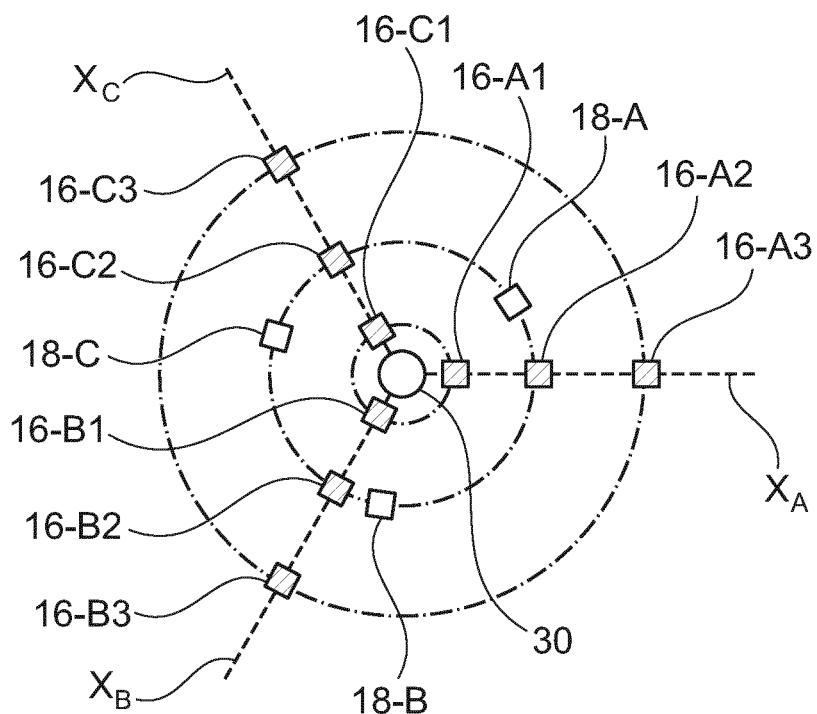
FIG. 7 shows an illustration of a light sources arrangement which can be used in a system for determining the prescription of an eye according to a third embodiment of the invention.

FIG. 7 illustrates a third embodiment of the system according to the invention. This third embodiment differs from the previous ones in that the system comprises a plurality of sets n of three first light sources 16-Ai, 16-Bi and 16-Ci for i an integer between 1 and n. Each first light source is adapted to illuminate the eye 2 of the person with respectively first light 20 having the first optical wavelength.

For each set i, the first light sources 16-Ai, 16-Bi and 16-Ci are arranged to be equidistant from the camera 30. Of course, the distance between the camera and the first light sources of a set is different from one set to another. The first light sources of the sets are arranged on the three meridians $X_A$, $X_B$ and $X_C$.

In this third embodiment, the system comprises a plurality of second light sources adapted to emit light having the second optical wavelength, preferably three second light sources 18-A, 18-B, 18-C as illustrated on FIG. 7.

The three second light sources 18-A, 18-B, 18-C are equidistant from the camera and are preferably regularly angularly spaced.

The three second light sources 18-A, 18-B, 18-C are arranged at the same distance from the camera than a set of three first light sources.

Each second light source 18-A, 18-B, 18-C is associated to one different meridian $X_A$, $X_B$ and $X_C$.

According to this third embodiment, all the measurements at the first wavelength are done before the single measurement at the second wavelength. Thus, the processor 44 is arranged to execute a program instructions stored in the memory to measure the photorefraction of the eye at the first wavelength by illuminating the eye with first light emitted successively by each first light source of at least one set of the plurality of sets before measuring the photorefraction of the eye at the second wavelength by illuminating the eye with second light emitted by the second light source.

Advantageously, the processor may be further arranged to execute a program instructions stored in the memory to implement a step S40 for selecting one of the second light sources to illuminate the eye before the measurement of the photorefraction of the eye at the second wavelength based on the measurement of the photorefraction of the eye at the first wavelength. Indeed, a first estimate of the eye refraction can be obtained from the first photorefraction measuring step S14 allowing to define a strategy for selecting the visible source to switch on. For example, the second light source associated to the meridian for which the infrared measurement is the most precise may be selected to have best accuracy for visible measurement.

Such third embodiment allows an accurate measurement of eye refraction at infrared wavelength thanks to the measurements in three directions $X_A$, $X_B$ and $X_C$ and for several distances between the set of first light sources and the camera and consequently, an accurate determining of the prescription for the eye of the person. Indeed, thanks to the measurements in three directions $X_A$, $X_B$ and $X_C$ the complete refraction may be determined, i.e. power, astigmatism and axis.

In addition, the use of several sets of first light sources at different distances from the camera allows a more precise first refraction measurement and thus a more accurate determination of the prescription especially when this one is important.

Figure 9:
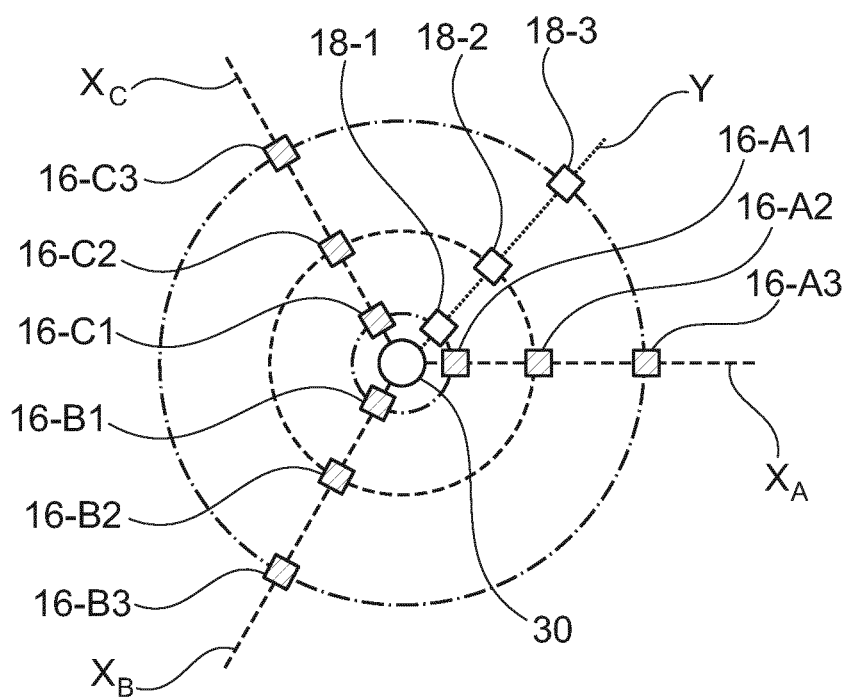
FIG. 9 shows an illustration of a light sources arrangement which can be used in a system for determining the prescription of an eye according to a fourth embodiment of the invention.

FIG. 9 shows a fourth embodiment of the system according to the invention compatible with the previous one. This fourth embodiment differs from the third embodiment in that the system comprises a plurality of second light sources 18-i adapted to emit light having the second optical wavelength and arranged in another way which will be detailed hereinafter.

Three second light sources 18-1, 18-2, 18-3 are illustrated on FIG. 9.

Each second light source 18-i is associated to a set i of three first light sources 16-Ai, 16-Bi, 16-Ci and is thus arranged at the same distance from the camera 30 than all the three first light sources of the set i. Thus, each second light source 18-1, 18-2, 18-3 is arranged at different distance from the camera 30.

Figure 8:
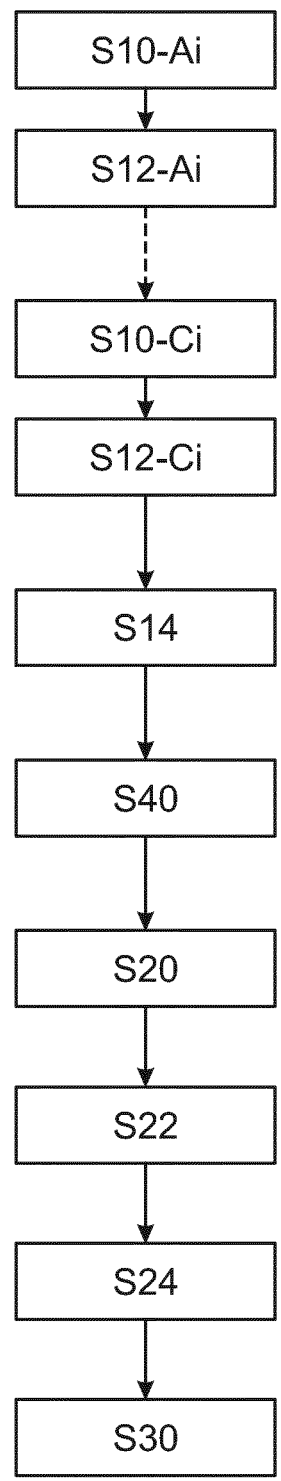
FIG. 8 is an illustration of a chart-flow of a method for determining a prescription of an eye of a person according to the third and a fourth embodiments of the invention.

According to this fourth embodiment, with reference to the flow chart in FIG. 8, the processor may be advantageously further arranged to execute a program instructions stored in the memory to implement a step S40 for selecting one of the second light sources to illuminate the eye before the measurement of the photorefraction of the eye at the second wavelength based on the measurement of the photorefraction of the eye at the first wavelength. Indeed, a first estimate of the eye refraction can be obtained from the first photorefraction measuring step S14 allowing to define a strategy for selecting the visible source to switch on. For example, the second light source arranged at a distance from the camera providing a measurement for which the eye refraction is not in the dark zone, based on the first refraction measurement may be selected to have best accuracy for visible measurement, and taking into account the intrinsic chromatism of the eye between first light and second light and more particularly in the case of infrared light and visible light.

Such fourth embodiment allows an accurate measurement of eye refraction at infrared wavelength thanks to the measurements in three directions $X_A$, $X_B$ and $X_C$ and for several distances between the set of first light sources and the camera and consequently, an accurate determining of the prescription for the eye of the person. Indeed, thanks to the measurements in three directions $X_A$, $X_B$ and $X_C$ the complete refraction may be determined, i.e. power, astigmatism and axis.

In addition, the use of several sets of first and second light sources at different distances from the camera allows more precise refraction measurements and thus a more accurate determination of the prescription especially when this one is important.

Another object of the invention is a method for providing an ophthalmic lens adapted to a prescription of the wearer, the method comprising:
determining a prescription for an eye of the wearer according to the invention and as previously described; and
manufacturing the ophthalmic lens according to the determined prescription adapted to the eye of the wearer.

The invention as disclosed hereinbefore has the advantage to provide a non-invasive, easy-to-use, cheap tool to perform e-refraction measurements, particularly in developing countries.

Indeed, the combination of measurements at two wavelengths and more particularly with an infrared light source to get large pupil and with a visible light source allows an accurate determination of the prescription for an eye of a person.

In addition, the invention can be easily performed on children and thus can provide a simple system for parents that want to monitor the evolution of the prescription of their children.

Furthermore, the invention allows measuring accurately the interpupillary distance of a person which is a very important parameter to provide to a wearer an appropriate pair of eyeglasses.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

Indeed, while in the disclosed embodiments, the acquisitions corresponding to each light source is performed sequentially, some of the acquisitions could be performed simultaneously to decrease the measurement time.

Alternatively, the first light sources may be infrared sources and the second light sources may be configured to emit blue light at around 550 nm. In this case, a weighted average of the measured refraction with both wavelengths corresponds to the real refraction and thus to the good prescription.

According to another embodiment, the system may comprise waveguides associated to some of the first and/or second light sources, for instance the most central light sources, so as to fictitiously bring the light sources closer to the camera.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A system for determining a prescription for an eye of a person, the system being configured to communicate with a mobile device, comprising:
at least one first light source adapted to illuminate the eye with first light having a first optical wavelength;
at least one second light source adapted to illuminate the eye with second light having a second optical wavelength different from the first wavelength;
at least one set of three first light sources, each adapted to emit first light at the first optical wavelength, said first light sources of each set being equidistant from a camera configured to record at least one picture of the eye of the person when the eye is illuminated by first light or second light and being arranged to define three directions regularly spaced angularly,
a processor; and
a memory storing program instructions that when executed by the processor causes the processor to be configured to:
measure photorefraction of the eye at the first wavelength based on at least one picture of the eye recorded when illuminating the eye with first light,
measure the photorefraction of the eye at the second wavelength based on at least one picture of the eye recorded when illuminating the eye with second light, and
determine the prescription for the eye based on the measured photorefraction at the first wavelength and the measured photorefraction at the second wavelength.

2. The system according to claim 1, wherein the processor and memory are embedded into the mobile device.

3. The system according to claim 1, wherein the processor is further configured to be in communication with a distant device including a second memory and a second processor, the second memory including program instructions that when executed by the second processor cause the second processor to be configured to store data relative at least to the measured photorefraction of the eye at the first wavelength, the measured photorefraction of the eye at the second wavelength.

4. The system according to claim 1, wherein the system is configured to be removably fastened to a housing of the mobile device.

5. The system according to claim 1, wherein each first light source is configured to emit infrared or near infrared light and each second light source is configured to emit visible light.

6. The system according to claim 1, wherein the second light source is arranged at a same distance as the first light source from a camera configured to record at least one picture of the eye of the person when the eye is illuminated by first light or second light.

7. The system according to claim 1, wherein the processor is further configured to:
- illuminate the eye with first light emitted successively by each first light source emitting at the first wavelength,
- illuminate the eye with second light by the second light source emitting at the second wavelength, and
- recording at least one picture of the eye of the person by a camera adapted and configured to record at least one picture of the eye of the person when the eye is illuminated by first light or second light.

8. A system for determining a prescription for an eye of a person, the system being configured to communicate with a mobile device, comprising:
- at least one first light source adapted to illuminate the eye with first light having a first optical wavelength;
- at least one second light source adapted to illuminate the eye with second light having a second optical wavelength different from the first wavelength;
- a processor; and
- a memory storing program instructions that when executed by the processor causes the processor to be configured to:
  - measure photorefraction of the eye at the first wavelength based on at least one picture of the eye recorded when illuminating the eye with first light,
  - measure the photorefraction of the eye at the second wavelength based on at least one picture of the eye recorded when illuminating the eye with second light, and
  - determine the prescription for the eye based on the measured photorefraction at the first wavelength and the measured photorefraction at the second wavelength,
- wherein the system further comprises a plurality of sets of three first light sources, each adapted to emit first light at the first optical wavelength, a distance between a camera and the first light sources of a set is different from one set to another, the first light sources of the plurality of the sets are arranged to define the same three directions regularly spaced angularly, and
- wherein the processor is further configured to measure the photorefraction of the eye at the first wavelength by illuminating the eye with first light emitted successively by each first light source of at least one set of the plurality of sets before measuring the photorefraction of the eye at the second wavelength by illuminating the eye with second light emitted by the second light source.

9. The system according to claim 8, wherein the processor and memory are embedded into the mobile device.

10. The system according to claim 8, wherein the processor is further configured to be in communication with a distant device including a second memory and a second processor, the second memory including program instructions that when executed by the second processor cause the second processor to be configured to store data relative at least to the measured photorefraction of the eye at the first wavelength, the measured photorefraction of the eye at the second wavelength.

11. The system according to claim 8, wherein the system is configured to be removably fastened to a housing of the mobile device.

12. The system according to claim 8, wherein each first light source is configured to emit infrared or near infrared light and each second light source is configured to emit visible light.

13. The system according to claim 8, wherein the second light source is arranged at a same distance as the first light source from a camera configured to record at least one picture of the eye of the person when the eye is illuminated by first light or second light.

14. The system according to claim 8, wherein the processor is further configured to:
- illuminate the eye with first light emitted successively by each first light source emitting at the first wavelength,
- illuminate the eye with second light by the second light source emitting at the second wavelength, and
- recording at least one picture of the eye of the person by a camera adapted and configured to record at least one picture of the eye of the person when the eye is illuminated by first light or second light.

15. A method for determining a prescription for an eye of a person with a system for determining a prescription for an eye of a person, the system being configured to communicate with a mobile device the system including at least one first light source adapted to illuminate the eye with first light having a first optical wavelength, at least one second light source adapted to illuminate the eye with second light having a second optical wavelength different from the first wavelength, at least one set of three first light sources, each adapted to emit first light at the first optical wavelength, said first light sources of each set being equidistant from a camera configured to record at least one picture of the eye of the person when the eye is illuminated by first light or second light and being arranged to define three directions regularly spaced angularly and a processor, the method comprising:
- measuring photorefraction of the eye at the first wavelength based on at least one picture of the eye recorded when illuminating the eye with first light emitted successively by each first light source;
- measuring the photorefraction of the eye at the second wavelength based on at least one picture of the eye recorded when illuminating the eye with second light emitted by the second light source; and
- determining the prescription for the eye based on the measured photorefraction at the first wavelength and the measured photorefraction at the second wavelength.

16. The method according to claim 15, further comprising determining a distance between the eye of the person and a camera.

17. A method for providing an ophthalmic lens adapted to a prescription of a wearer, the method comprising:
- determining a prescription for an eye of the wearer according to claim 15; and
- manufacturing the ophthalmic lens according to the determined prescription adapted to the eye of the wearer.

18. A method for determining a prescription for an eye of a person with a system for determining a prescription for an eye of a person, the system being configured to communicate with a mobile device the system including at least one first light source adapted to illuminate the eye with first light having a first optical wavelength, at least one second light source adapted to illuminate the eye with second light having a second optical wavelength different from the first wavelength, a plurality of sets of three first light sources, each adapted to emit first light at the first optical wavelength, a distance between a camera and the first light sources of a set is different from one set to another, the first light sources of the plurality of the sets are arranged to define the same three directions regularly spaced angularly, and a processor, said processor being configured to measure a photorefraction of the eye at the first wavelength by illuminating the eye with first light emitted successively by each first light source of at least one set of the plurality of sets before measuring the photorefraction of the eye at the second wavelength by illuminating the eye with second light emitted by the second light source, the method comprising:

measuring photorefraction of the eye at the first wavelength based on at least one picture of the eye recorded when illuminating the eye with first light emitted successively by each first light source;

measuring the photorefraction of the eye at the second wavelength based on at least one picture of the eye recorded when illuminating the eye with second light emitted by the second light source; and determining the prescription for the eye based on the measured photorefraction at the first wavelength and the measured photorefraction at the second wavelength.

19. The method according to claim 18, further comprising determining a distance between the eye of the person and a camera.

20. A method for providing an ophthalmic lens adapted to a prescription of a wearer, the method comprising:

determining a prescription for an eye of the wearer according to claim 18; and manufacturing the ophthalmic lens according to the determined prescription adapted to the eye of the wearer.

\* \* \* \* \*